US008521255B2

(12) United States Patent
DiSilvestro et al.

(10) Patent No.: US 8,521,255 B2
(45) Date of Patent: *Aug. 27, 2013

(54) REGISTRATION POINTER AND METHOD FOR REGISTERING A BONE OF A PATIENT TO A COMPUTER ASSISTED ORTHOPAEDIC SURGERY SYSTEM

(75) Inventors: Mark R. DiSilvestro, Columbia City, IN (US); Jason T. Sherman, Warsaw, IN (US); Edward J. Caylor, III, Fort Wayne, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/983,676

(22) Filed: Jan. 3, 2011

(65) Prior Publication Data

US 2011/0098577 A1    Apr. 28, 2011

Related U.S. Application Data

(62) Division of application No. 11/428,078, filed on Jun. 30, 2006, now Pat. No. 7,885,701.

(51) Int. Cl.
*A61B 5/05* (2006.01)
(52) U.S. Cl.
USPC ......................................... 600/407; 600/427
(58) Field of Classification Search
USPC ................................................ 600/407, 427
See application file for complete search history.

(56) References Cited

U.S. PATENT DOCUMENTS

| | | | |
|---|---|---|---|
| 5,023,725 | A | 6/1991 | McCutchen |
| 5,230,623 | A | 7/1993 | Guthrie et al. |
| 6,337,708 | B1 | 1/2002 | Furlan et al. |
| 6,611,282 | B1 | 8/2003 | Trubko et al. |
| 2005/0015005 | A1 | 1/2005 | Kockro |
| 2005/0128184 | A1 | 6/2005 | McGreevy |
| 2006/0020213 | A1 | 1/2006 | Whitman et al. |
| 2006/0030753 | A1 | 2/2006 | Boutillette et al. |
| 2006/0084867 | A1 | 4/2006 | Tremblay et al. |

FOREIGN PATENT DOCUMENTS

| | | |
|---|---|---|
| EP | 1580986 | 9/2005 |
| WO | 2005/013001 | 2/2005 |
| WO | 2007/011306 | 1/2007 |

OTHER PUBLICATIONS

Partial European Search Report for European Patent Application No. 07252633.8-2310 / 1872737, Feb. 18, 2009, 11 pgs.

*Primary Examiner* — Unsu Jung
*Assistant Examiner* — Saurel J Selkin
(74) *Attorney, Agent, or Firm* — Barnes & Thornburg LLP

(57) ABSTRACT

A registration pointer includes a camera located in an elongated shaft having a distal end configured to be contacted to a bone of a patient to register the bone to a computer assisted orthopaedic surgery system. The camera may be a hemispherical camera and may include a panoramic camera and a wide-angle camera equipped with a fish-eye lens. The registration pointer is configured to transmit images received by the cameras to the computer assisted orthopaedic surgery system for display thereon. The computer assisted orthopaedic surgery system may be configured to generate an image, such as a hemispherical image, based on the images received from the registration pointer.

20 Claims, 10 Drawing Sheets

REGISTRATION POINTER AND METHOD FOR REGISTERING A BONE OF A PATIENT TO A COMPUTER ASSISTED ORTHOPAEDIC SURGERY SYSTEM

This application is a divisional application of U.S. patent application Ser. No. 11/428,078, filed on Jun. 30, 2006 and issued as U.S. Pat. No. 7,885,701 on Feb. 8, 2011,which is incorporated herein by reference.

TECHNICAL FIELD

The present disclosure relates generally to computer assisted surgery systems for use in the performance of orthopaedic surgical procedures and, more particularly, to devices and methods for registering bones of a patient to computer assisted surgery systems.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation.

Computer assisted orthopaedic surgery (CAOS) systems assist surgeons in the performance of orthopaedic surgical procedures by, for example, displaying images illustrating surgical steps of the surgical procedure being performed and rendered images of the relevant bones of the patient. Before a computer assisted orthopaedic surgery (CAOS) system can display a rendered image of a bone, the bone must first be registered with the computer assisted orthopaedic surgery (CAOS) system. Registering the bone with the computer assisted orthopaedic surgery (CAOS) system allows the system to determine the relevant contour, location, and orientation of the bone and display the rendered image according to such parameters. In typical computer assisted orthopaedic surgery (CAOS) systems, a bone is registered by touching a number of locations on the surface of the bone with a tip of a registration pointer. Based on a determined location of the registration pointer, the locations of the surface of the bone are computed. The system may then generate a rendered image of the bone, including the contour of the bone, based on such computed locations.

SUMMARY

According to one aspect, a registration pointer for registering a bone with a computer assisted surgery system may include an elongated shaft. The elongated shaft may have a distal end configured to be contacted to the bone. For example, the distal end may include a lens manufactured from an optical quality, industrial grade translucent gem-like material such as quartz, ruby, diamond, and/or the like that is configured to be contacted to the bone. The registration pointer may also include a camera located in the elongated shaft. The camera may be, for example, a hemispherical camera and, in some embodiments, may include a first camera and a second camera. The first camera may be a panoramic camera and/or the second camera may be a wide-angle camera. The panoramic camera may have a horizontal field of view of about 360 degrees and a vertical field of view of about 120 degrees when the elongated shaft is positioned on a vertical plane. The wide-angle camera may have a vertical field of view of about 60 degrees when the elongated shaft is positioned on a vertical plane. The wide-angle camera may include a fish-eye lens.

The registration pointer may also include a light source. The light source may be embodied as a light emitting diode located in the elongated shaft. Alternatively, the light source may be located outside the elongated shaft, such as in the handle of the registration pointer, and channeled into the elongated shaft via a suitable light conductor such as a fiber optic wire or cable. The registration pointer may also include a transmitter communicatively coupled to the camera and configured to transmit images received from the camera. The transmitter may be a wired or a wireless transmitter. The registration pointer may also include a button and a control circuit. The control circuit may be communicatively coupled to the camera and the button. The control circuit may be configured to store an image received from the camera in response to selection of the button by a user of the registration pointer.

According to another aspect, a computer assisted orthopaedic surgery system may include a registration pointer having a camera located at a distal end. The computer assisted orthopaedic surgery system may also include a display device and a processor communicatively coupled to the registration pointer and the display device. The computer assisted orthopaedic surgery system may further include a memory device electrically coupled to the processor. The memory device may have stored therein a plurality of instructions, which when executed by the processor, cause the processor to receive a first image and a second image from the registration pointer. The first image and the second image may be received via a wired and/or wireless communication link. The plurality of instructions may also cause the processor to generate a third image based on the first image and the second image. The third image may be, for example, a hemispherical image. Additionally, the plurality of instructions may also cause the processor to display the third image on the display device. The display device may be a computer screen, a display monitor, a heads-up display, and/or other type of display device. In some embodiments, the third image is superimposed on a rendered image of a bone.

In some embodiments, the camera may be a hemispherical camera. The hemispherical camera may include a first camera and a second camera. The first camera may be, for example, a panoramic camera. The second camera may be, for example, a wide-angle camera having a fish-eye lens. Additionally, the plurality of instructions may cause the processor to receive a signal from the registration pointer and store the third image based on the signal. The plurality of instructions may further cause the processor to receive position data indicative of a position of the registration pointer and display a rendered image of a bone on the display screen based on the position data.

According to yet another aspect, a method for displaying an image of a patient during the performance of an orthopaedic surgical procedure may include receiving a first image from a camera of a registration pointer. The first image may be received from, for example, a panoramic camera. The method may also include receiving a second image from a second camera of the registration pointer. The second image may be received from, for example, a wide-angle camera having a fish-eye lens. Additionally, the method may include generating a hemispherical image based on the first image and the second image and displaying the hemispherical image on a display device. The method may also include activating a light source of the registration pointer. Further, the method may include receiving a signal from the registration pointer and storing the hemispherical image based on the signal.

BRIEF DESCRIPTION OF THE DRAWINGS

The detailed description particularly refers to the following figures, in which.

DETAILED DESCRIPTION OF THE DRAWINGS

Figure 1:
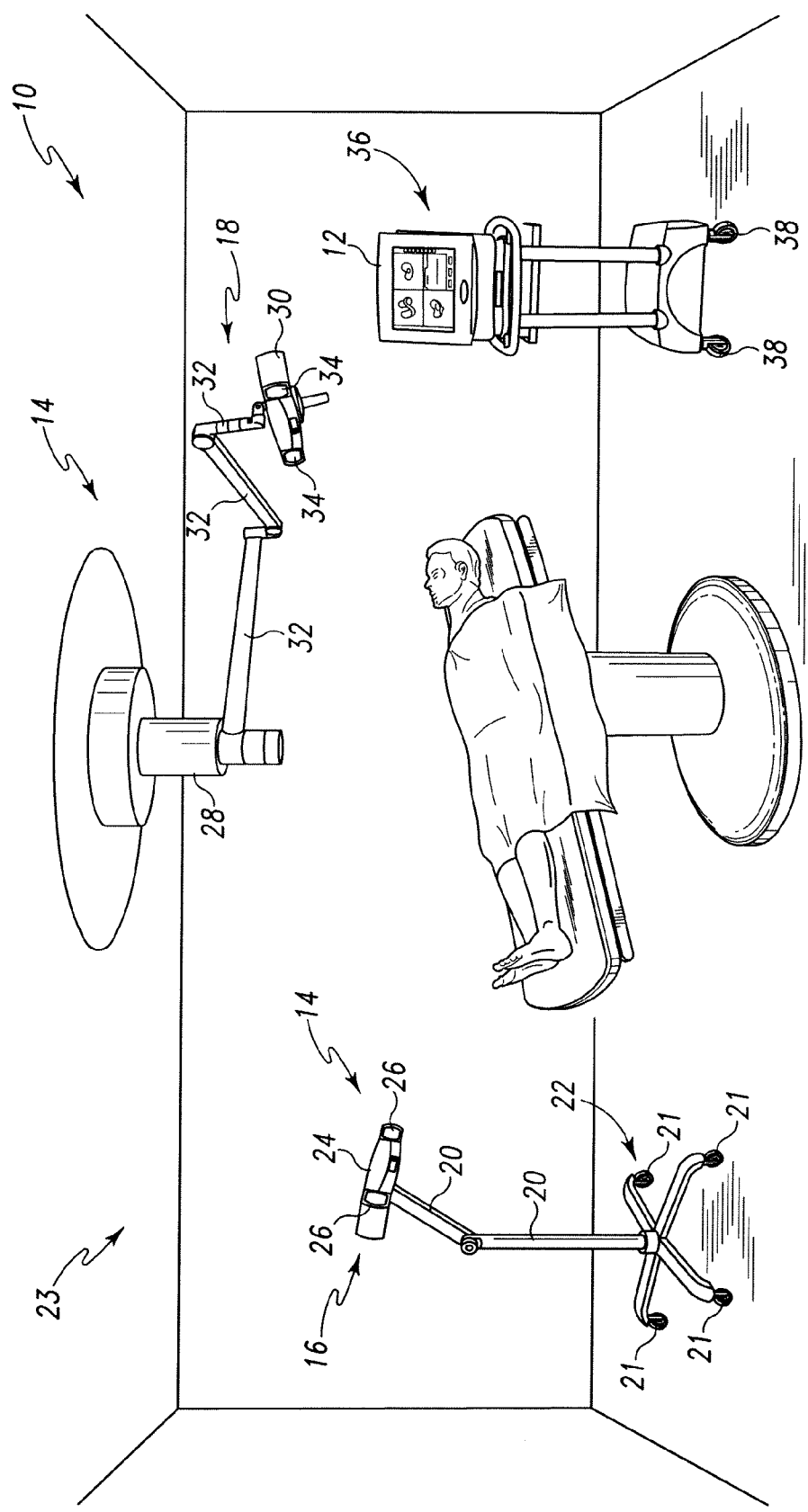
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as one or more computer assisted orthopaedic surgery systems commercially available from DePuy Orthopaedics, Inc. of Warsaw, Ind. and/or one or more computer assisted orthopaedic surgery systems commercially available from BrainLAB of Heimstetten, Germany. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 21 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 30 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
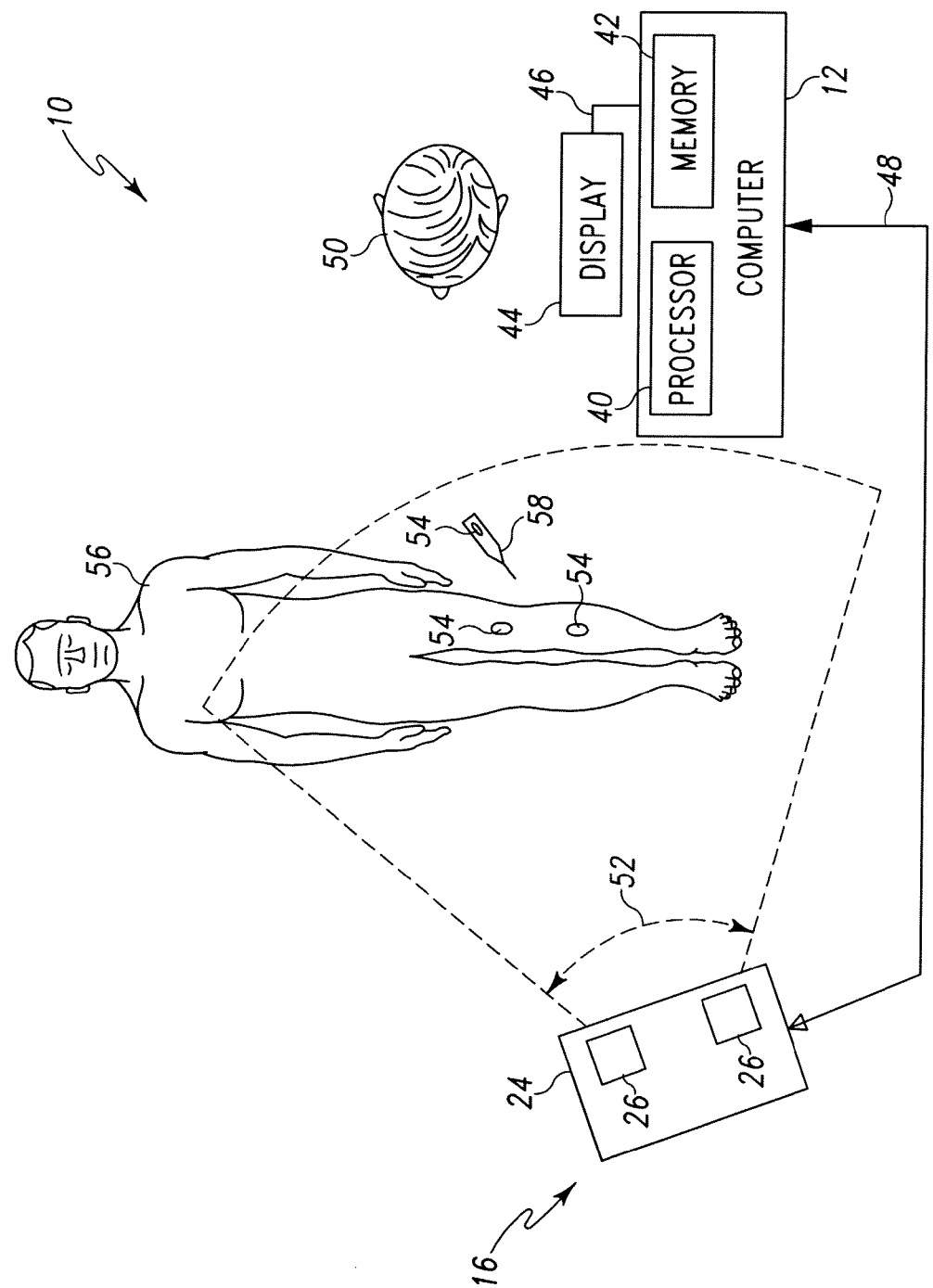
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
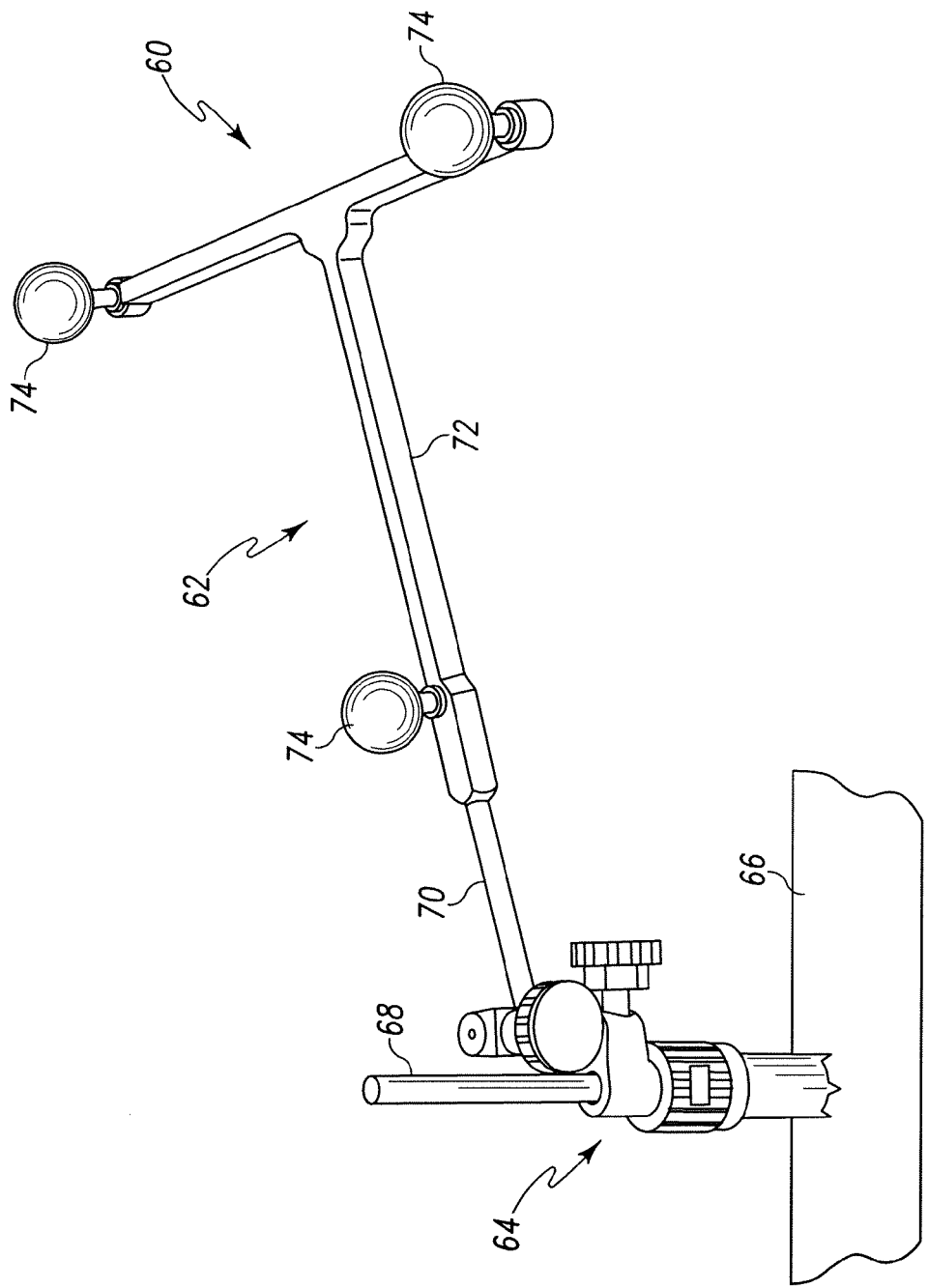
FIG. 3 is a perspective view of a bone locator tool.

The CAOS system 10 may also include a number of sensors or sensor arrays 54 which may be coupled the relevant bones of a patient 56 and/or with orthopaedic surgical tools 58. For example, as illustrated in FIG. 3, a tibial array 60 includes a sensor array 62 and bone clamp 64. The illustrative bone clamp 64 is configured to be coupled with a tibia bone 66 of the patient 56 using a Schantz pin 68, but other types of bone clamps may be used. The sensor array 62 is coupled with the bone clamp 64 via an extension arm 70. The sensor array 62 includes a frame 72 and three reflective elements or sensors 74. The reflective elements 74 are embodied as spheres in the illustrative embodiment, but may have other geometric shapes in other embodiments. Additionally, in other embodiments sensor arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
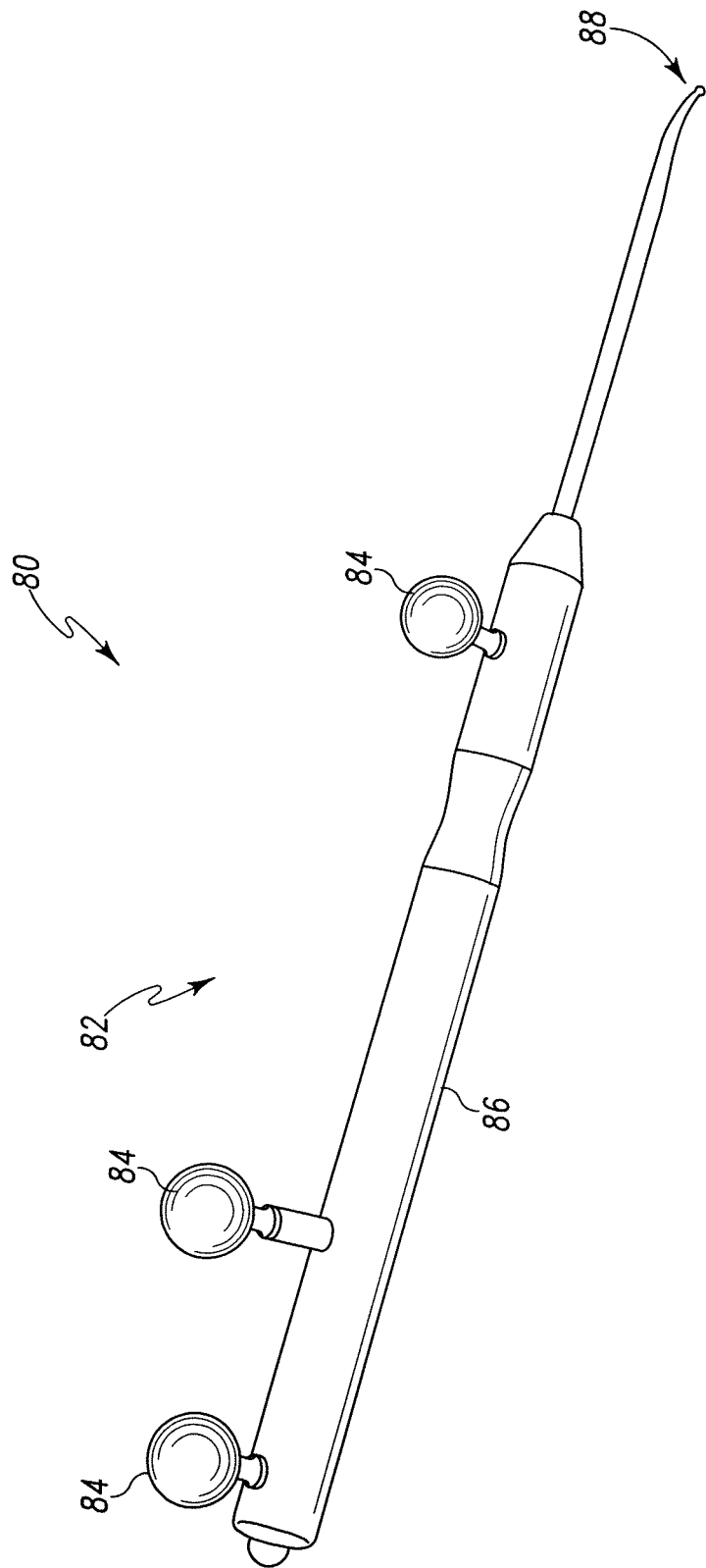
FIG. 4 is a perspective view of a registration tool for use with the system of FIG. 1.
Figure 5:
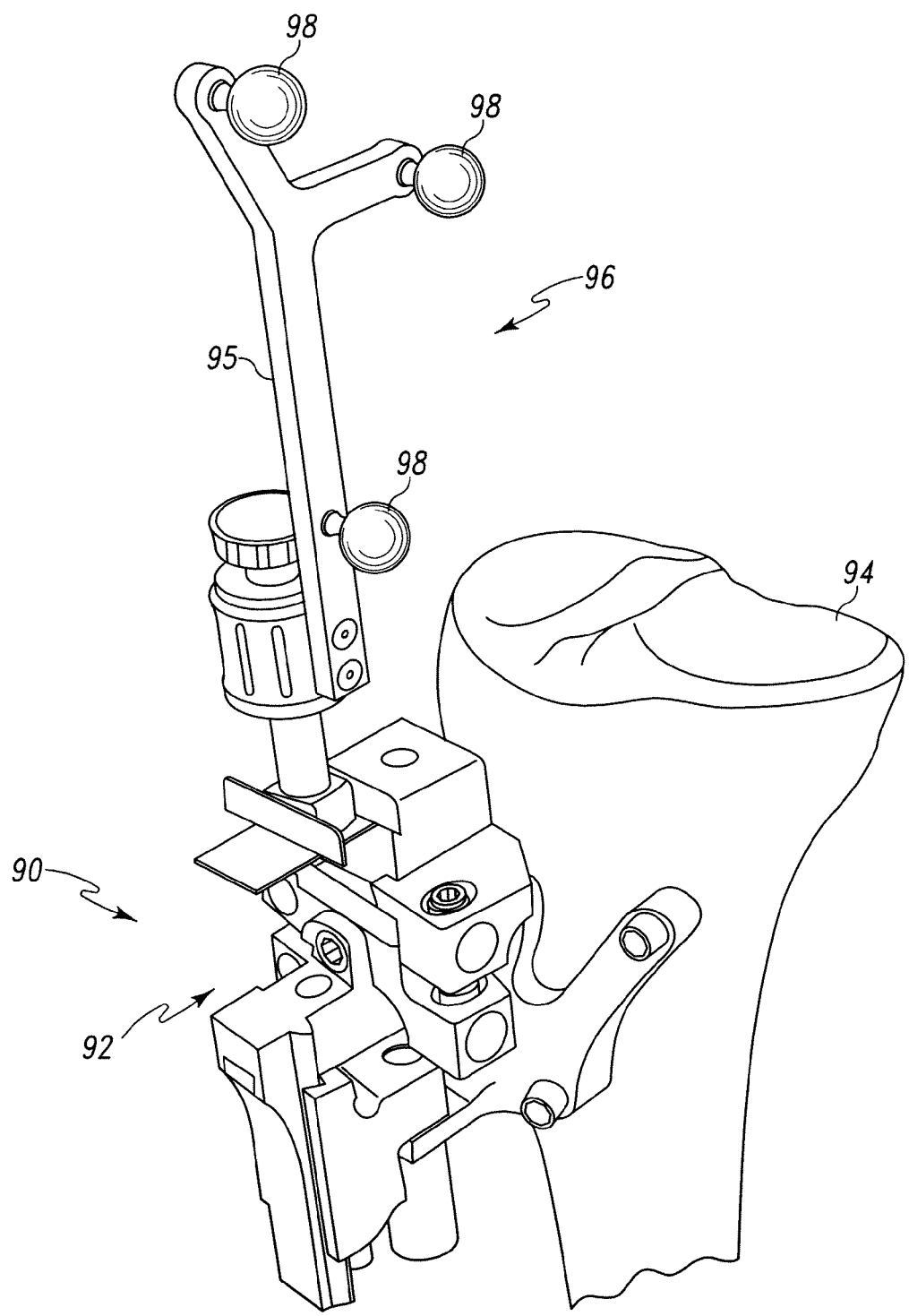
FIG. 5 is a perspective view of an orthopaedic surgical tool for use with the system of FIG. 1.

Sensor arrays may also be coupled to other surgical tools. For example, a registration tool 80, as shown in FIG. 4, is used to register points of a bone of the patient. The registration tool 80 includes a sensor array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, sensor arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a sensor array 96 that is coupled with the portion 92 via a frame 95. The sensor array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walkthrough" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the sensor arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
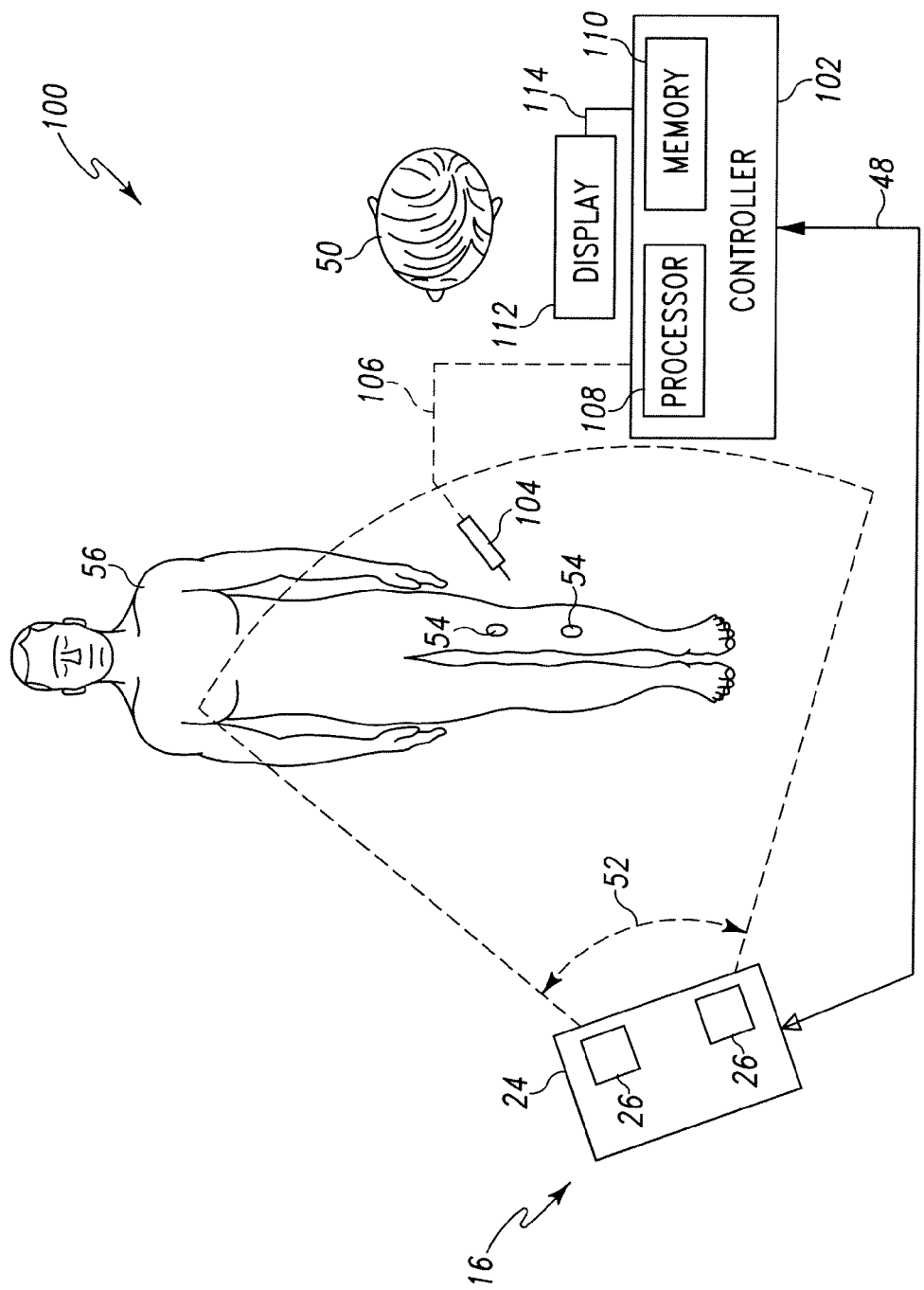
FIG. 6 is a simplified diagram of another computer assisted orthopaedic surgery (CAOS) system.
Figure 10:
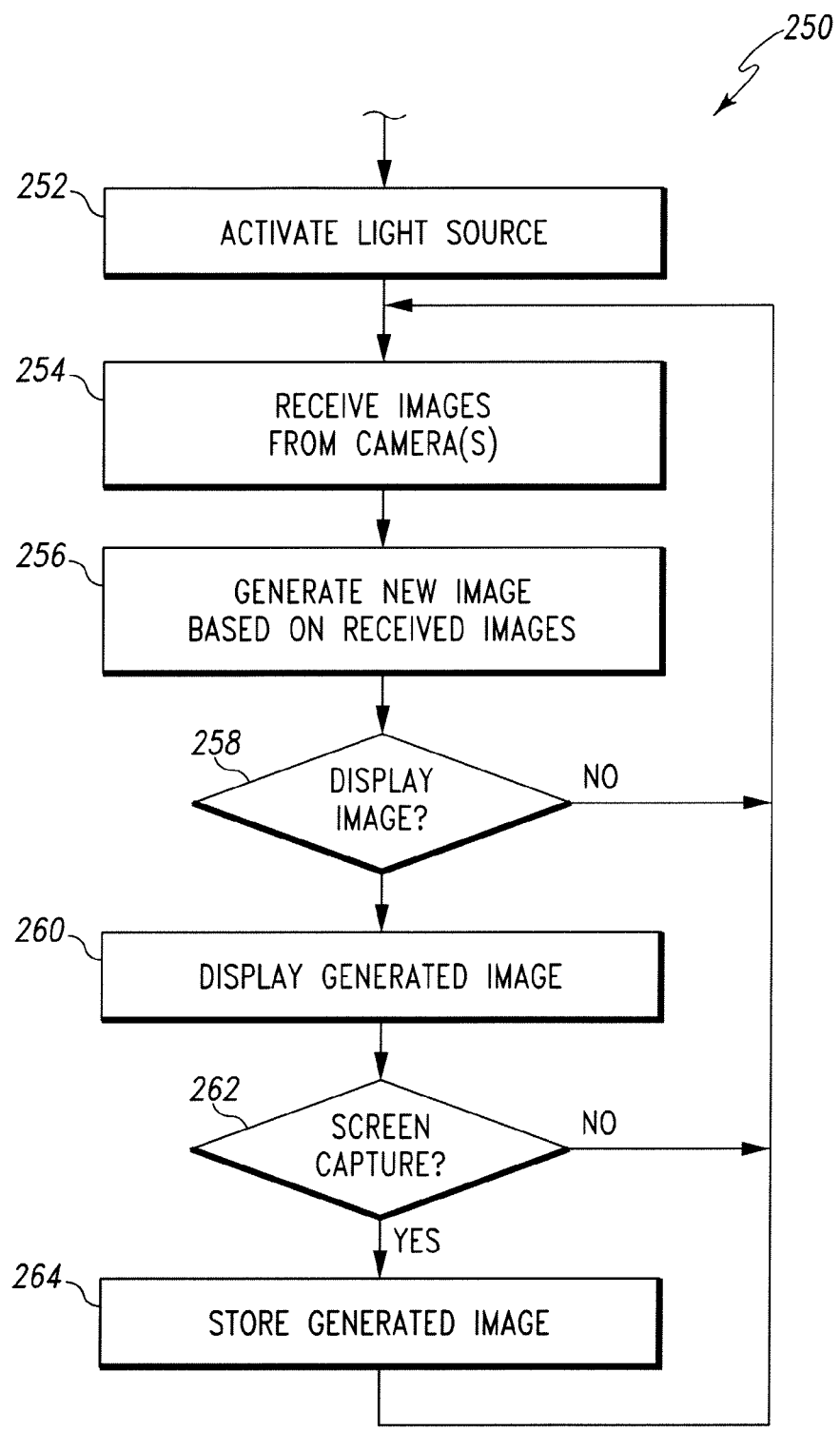
FIG. 10 is a simplified flow chart of an algorithm for registering a bone of a patient to a computer assisted orthopaedic surgery system.

Referring now to FIG. 6, in another embodiment, a computer assisted orthopaedic surgery (CAOS) system 100 includes a controller 102 and a registration pointer 104. The controller 102 is communicatively coupled to the registration pointer 104 via a communication link 106. As discussed in more detail below in regard to FIG. 10, the communication link 106 may be embodied as any type of communication link capable of facilitating communication between the controller 102 and the registration pointer 104. For example, the communication link 106 may be a wired communication link and embodied as any number of wires, cables, or the like. Alternatively, the communication link 106 may be a wireless communication link. In such embodiments, the registration pointer 104 may use any suitable wireless communication technology and protocol to communicate with the controller 102 via the communication link 106 such as, for example, a Bluetooth wireless communication protocol, a wireless local area network (WLAN) communication protocol, or the like.

The controller 102 includes a processor 108 and a memory device 110. The processor 108 may be embodied as any type of processor including, for example, discrete processing circuitry (e.g., a collection of logic devices), general purpose integrated circuit(s), and/or application specific integrated circuit(s) (i.e., ASICs). The memory device 110 may be embodied as any type of memory device and may include one or more memory types, such as, random access memory (i.e., RAM) and/or read-only memory (i.e., ROM). In addition, the controller 102 may include other devices and circuitry typically found in a computer for performing the functions described herein such as, for example, a hard drive, input/output circuitry, and the like.

The controller 102 is communicatively coupled with a display device 112 via a communication link 114. Although illustrated in FIG. 6 as separate from the controller 102, the display device 112 may form a portion of the controller 102 in some embodiments. Additionally, in some embodiments, the display device 112 or an additional display device may be positioned away from the controller 102. For example, the display device 112 may be coupled to the ceiling or wall of the operating room wherein the orthopaedic surgical procedure is to be performed. Additionally or alternatively, the display device 112 may be embodied as a virtual display such as a holographic display, a body mounted display such as a heads-up display, or the like. The controller 102 may also be coupled with a number of input devices such as a keyboard and/or a mouse for providing data input to the controller 102. However, in the illustrative embodiment, the display device 112 is a touch-screen display device capable of receiving inputs from the orthopaedic surgeon 50 similar to the display device 44 described above in regard to FIG. 2. That is, the surgeon 50 can provide input data to the controller 102, such as making a selection from a number of on-screen choices, by simply touching the screen of the display device 112.

Figure 7:
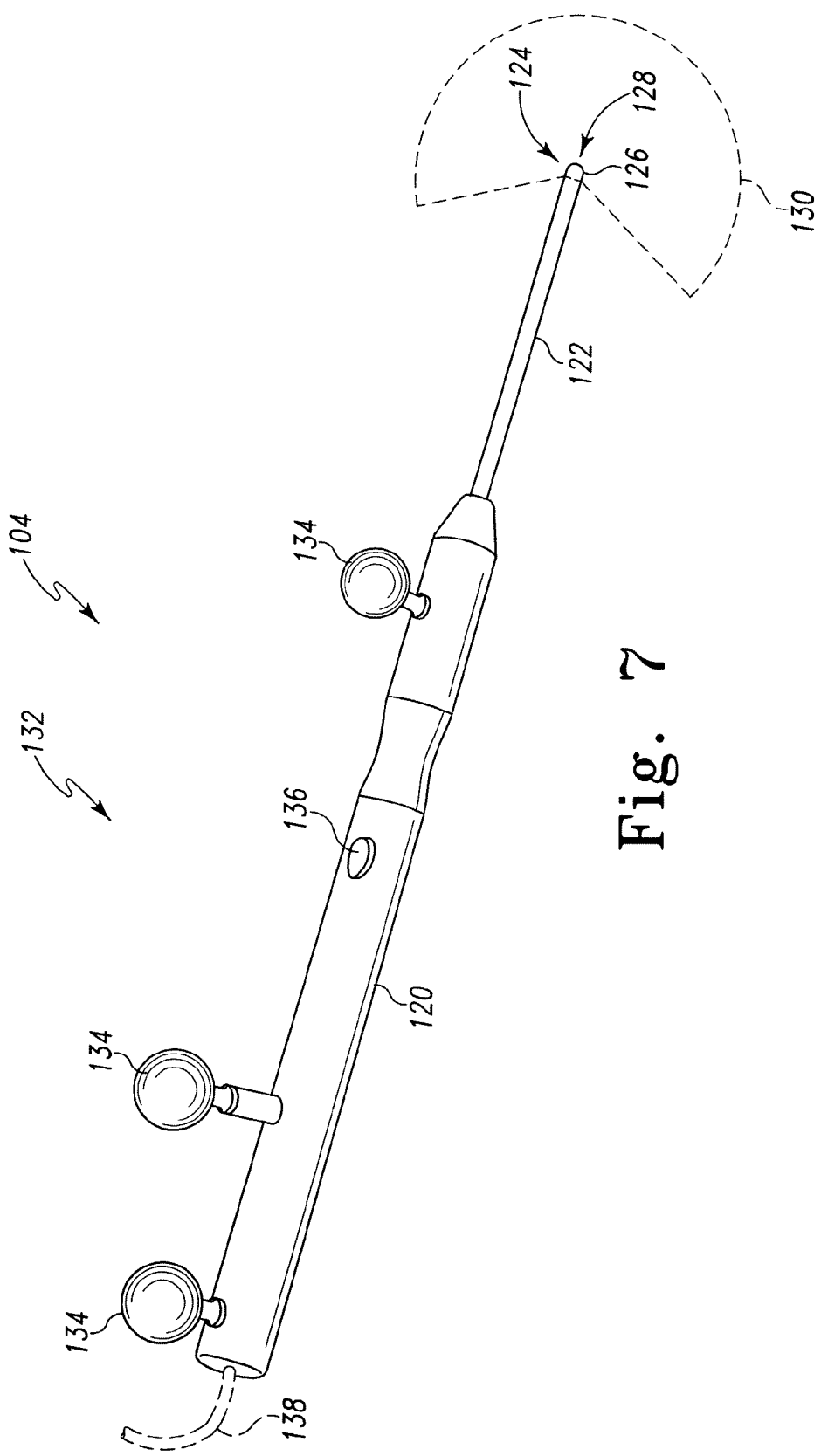
FIG. 7 is a perspective view of a registration pointer of the CAOS system of FIG. 6.

Referring now to FIG. 7, the illustrative registration pointer 104 includes a handle 120 and an elongated shaft 122 extending therefrom. The elongated shaft 122 includes a distal end 124 that is configured to be touched or otherwise contacted to locations on a surface of a bone of a patient during a bone registration procedure as described above in regard to FIG. 4. The distal end 124 includes a lens 126 having a substantial hemispherical shape such that the geometric center of the lens 126 is approximately equidistant from each point on the hemispherical surface of the lens 126. As such, when the lens 126 is contacted to a bone of a patient, the distance from the geometric center of the lens 126 to the point of contact is approximately equal regardless of which point on the hemispherical surface of the lens 126 is contacted with the bone. The lens 126 may be formed from any transparent material having a substantial hardness such that the lens 126 may be repeatedly contacted with bone and other tissue of a patient without substantially deteriorating the transparency of the material. In one particular embodiment, the lens 126 is formed from crystal quartz. However, in other embodiments, other optical quality, industrial grade translucent gem-like material such as quartz, ruby, diamond, and/or the like may be used.

A camera 128 is positioned in the elongated shaft 122 toward the distal end 124. The camera 128 is so positioned such that a field of view 130 of the camera extends through the lens 126. As such, the registration pointer 104 is usable to register bones of a patient to the controller 102 in a manner as described above in regard to FIGS. 2 and 4 and provide images of the relevant bone and other anatomical structures of the patient via the camera 128. The camera 128 may be embodied as any type and number of cameras capable of being located in the registration tool 104 and providing the desired image, field of view, etc. In one particular embodiment, the camera 128 is embodied as a hemispherical camera configured to produce a number of images from which a hemispherical image may be generated. For example, as described in more detail below in regard to FIG. 8, the camera 128 may be embodied as a panoramic camera and a wide-angle camera.

The illustrative registration pointer 104 also includes a sensor array 132 embodied as a number of reflective elements 134. The reflective elements 134 are substantially similar to the reflective elements 84 illustrated in and described above in regard to FIG. 4. The reflective elements 134 are positioned in a predefined configuration that allows the controller 102 to determine the location and orientation of the registration pointer 104 based on images received from the camera 16.

In other embodiments, other types of sensors may be used to determine the location of the registration pointer 104. For example, in some embodiments, the registration pointer may include a magnetic or electromagnetic source such as a permanent magnet. In such embodiments, the location of the registration pointer 104 may be determined based on signals received from a number of magnetic sensors as described in more detail in U.S. patent application Ser. No. 11/323,609, entitled "APPARATUS AND METHOD FOR REGISTERING A BONE OF A PATIENT WITH A COMPUTER ASSISTED ORTHOPAEDIC SURGERY SYSTEM," U.S. patent application Ser. No. 11/323,963, entitled "SYSTEM AND METHOD FOR REGISTERING A BONE OF A PATIENT WITH A COMPUTER ASSISTED ORTHOPAEDIC SURGERY SYSTEM," U.S. patent application Ser. No. 11/323,537, entitled "METHOD FOR DETERMINING A POSITION OF A MAGNETIC SOURCE," and U.S. patent application Ser. No. 11/323,610, entitled "MAGNETIC SENSOR ARRAY," the entirety of each of which is expressly incorporated herein by reference.

Additionally or alternatively, the registration pointer 104 may include a magnetic or electromagnetic sensor. In such embodiments, the location of the registration pointer 104 may be determined based on the signals received by the magnetic and/or electromagnetic sensors as described in more detail in International Patent Application Number PCT/GB2005/000874, entitled "Registration Methods and Apparatus," and in International Patent Application Number PCT/GB2005/000933, entitled "Orthopaedic Operating Systems, Methods, Implants and Instruments", the entirety of each of which is expressly incorporated herein by reference. As such, it should be appreciated that the sensor array 132 may be embodied a number of reflective elements, a number of magnetic/electromagnetic sensors, and/or a number of magnetic/electromagnetic sources such as permanent magnets. Accordingly, as used herein, the term "sensor array" is intended to refer to any number of reflective sensors, magnetic and/or electromagnetic sensors, and/or magnetic and/or electromagnetic sources.

The registration pointer 104 may also include any number of user-selectable input devices 136. For example, the registration pointer 104 may include a button 136 selectable by a user of the registration pointer 104 to capture or otherwise save an image received by the camera 128 as discussed in more detail below in regard to FIG. 10. Although only a single button 136 is illustrated in FIG. 7, it should be appreciated that in other embodiments the registration pointer 104 may include any number of user-selectable input devices for controlling any one or more functions of the pointer 104. For example, in some embodiments, as discussed below in regard to FIG. 8, the registration pointer 104 may include a button or other input device selectable by a user of the pointer 104 to active a light source located in the elongated shaft 122 of the pointer 104. In embodiments wherein the communication link 106 is embodied as a wired communication link, the registration pointer 104 may also include a cable, wire, or other conductor 138 for communicatively coupling the pointer 104 to the controller 102.

Figure 8:
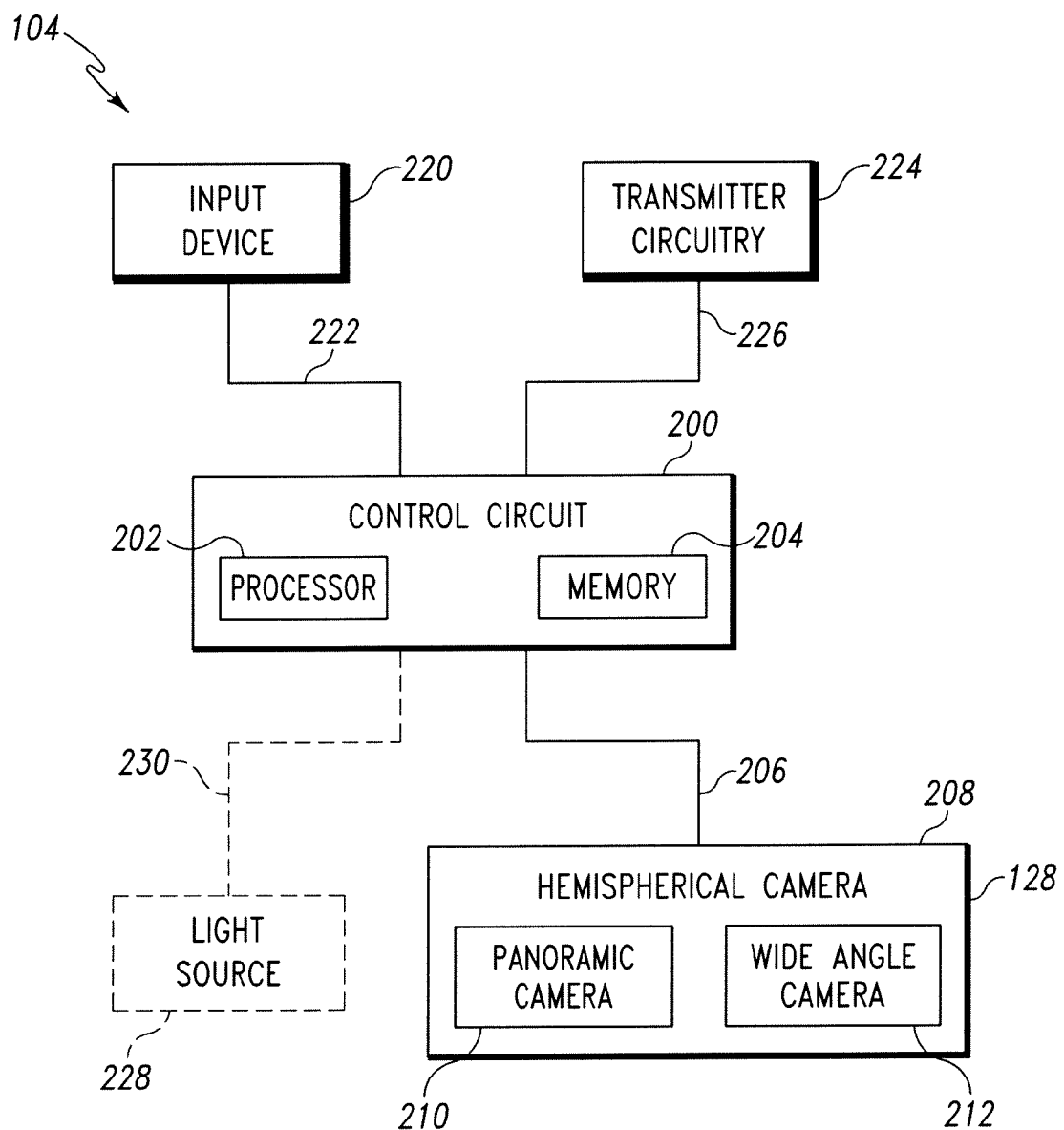
FIG. 8 is a side elevation view of a distal end of the registration pointer of FIG. 7.

As illustrated in FIG. 8, the registration pointer 104 also includes a control circuit 200. The control circuit 200 is located in the handle 120 of the registration pointer 104 and is configured to control the operations of the camera 128. The control circuit 200 includes a processor 202 and a memory device 204. The processor 202 may be embodied as any type of processor including, for example, discrete processing circuitry (e.g., a collection of logic devices), general purpose integrated circuit(s), and/or application specific integrated circuit(s) (i.e., ASICs). The memory device 204 may be embodied as any type of memory device and may include one or more memory types, such as, random access memory (i.e., RAM) and/or read-only memory (i.e., ROM).

Figure 9:
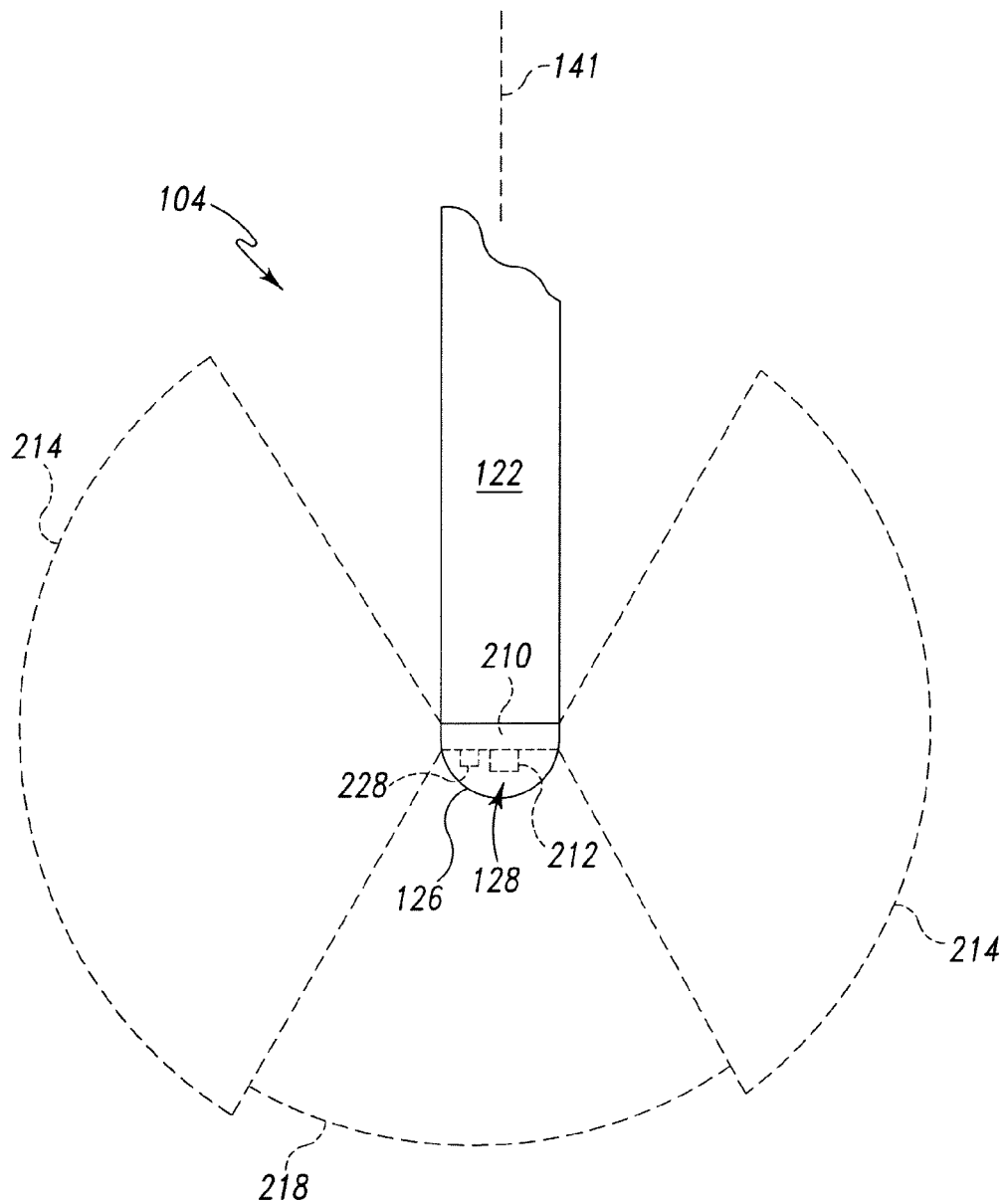
FIG. 9 is a simplified block diagram of an electrical circuit of the registration pointer of FIG. 7.

The control circuit 200 is electrically coupled to the camera 128 via a number of communication links 206 such as wires, printed circuit board traces, cables, or the like. In the illustrative embodiment, the camera 128 is embodied as a hemispherical camera 208 and includes a panoramic camera 210 and a wide-angle camera 212. As illustrated in FIG. 9, the cameras 210, 212 are located in the elongated shaft 122 and toward the distal end 124 such that the field of view of each camera extends through the lens 126. The panoramic camera 210 has a horizontal field of view of about 360 degrees and a vertical field of view 214 of about 120 degrees when the elongated shaft 122 of the registration pointer 104 is located in a vertical plane 216 as shown in FIG. 9. The wide-angle camera 212 includes a fish-eye lens and has a field of view 218 of about 60 degrees. The fields of view 214, 218 are substantially contiguous with each other in the illustrative embodiment. However, in other embodiments, cameras having fields of view of different magnitudes. In such embodiments, the fields of view 214, 218 of each camera overlap each other by a predetermined amount. Such overlap is calibrated or otherwise accounted for when generating the hemispherical image based on the images received from each camera 210, 212 as discussed below in regard to FIG. 10.

Referring back to FIG. 8, the control circuit 200 is also communicatively coupled to one or more input devices 220 via a number of communication links 222. The communication links 222 may be embodied as any type of communication links, such as wires, cables, printed circuit board traces, and the like, capable of facilitating communication between the input devices 220 and the control circuit 200. The input devices 220 may be embodied as any type of input devices selectable by a user of the registration pointer 104. For example, the input device 220 may be embodied as a button, such as the button 136 illustrated in FIG. 7, a switch, or other device selectable by the user. Any number of input devices 220 may be included and may be selected by the user to provide a request signal to the control circuit 200. For example, in one embodiment, one of the input devices 220 is selectable by a user to cause the control circuit 200 to capture or otherwise store an image received from the hemispherical camera 208. The image may be saved in the memory device 204 of the control circuit 200 and/or the memory 110 of the controller 102.

A transmitter circuit 224 is also included in the registration pointer 104. The transmitter 224 is communicatively coupled to the control circuit 200 via a number of communication links 226. The communication links 226 may be similar to the communication links 222 and may be embodied as any type of communication links, such as wires, cables, printed circuit board traces, and the like, capable of facilitating communication between the transmitter circuit 224 and the control circuit 200. The transmitter circuit 224 may be embodied as any number of electrical devices configured to transmit any number of images received from the hemispherical camera 208 to the controller 102 via the communication link 106. For example, the transmitter circuit 224 may be a wired transmitter configured to transmit the images over a wired communication link 106. Alternatively, in embodiments wherein the communication link 106 is a wireless communication link, the transmitter circuit 224 may be embodied as a wireless transmitter and may use any suitable transmission protocol, such as a Bluetooth communication protocol, a wireless local area network communication protocol, or the like, to transmit the images from the registration pointer 104 to the controller 102.

In some embodiments, the registration pointer 104 may also include one or more light sources 228. In such embodiments, the light sources 228 are communicatively coupled to the control circuit 200 via a number of communication links 230 such as such as wires, cables, printed circuit board traces, and the like. The light source may be embodied as any type of light source capable of producing enough light such that the hemispherical camera 208 (i.e., cameras 210, 212) is capable of producing images that may be viewed by a user. In one particular embodiment, the light source 228 is embodied a light emitting diode (LED), but other light emitting devices may be used in other embodiments. As illustrated in FIG. 9, the light source 228 is also located in the elongated shaft 122 and toward the distal end 124 such that light emitting from the light source 228 extends through the lens 126.

In operation, the registration pointer 104 may be used by a surgeon or other healthcare provider during an orthopaedic surgical procedure to register a bone of a patient with the controller 102. In addition, at any time during the surgical procedure, the surgeon may use the registration pointer 104 to view the anatomy of the patient. To do so, the controller 102 may execute an algorithm 250 for displaying an image of a patient during the performance of the orthopaedic surgical procedure. The algorithm 250 begins with process step 252 in which a light source is activated in the region desired to be viewed by the surgeon. In embodiments wherein the registration pointer 104 includes the light source 228, such as a LED, the light source 228 may be activated in process step 252. To do so, the surgeon or other healthcare provider may select the appropriate input device 220. In response, the control circuit 200 is configured to activate the light source 228 via a signal supplied on the communication link 230. Alternatively or additionally, the surgeon may activate the light source 228 or other light source by supplying the appropriate command to the controller 102 via the display 112 (in embodiments wherein the display 112 is a touch screen display) or via other input device(s) such as a keyboard. In response, the controller 102 is configured to transmit a signal to the registration pointer 104 via the communication link 106 to activate the light source 228.

Next, in process step 254, images are received from the hemispherical camera 208 (i.e., from the panoramic camera 210 and from the wide angle camera 212) and a new image, such as a hemispherical image, is generated based on such images in process step 256. The images from the cameras 210, 212 may be received by the control circuit 200 and/or the controller 102. That is, in one embodiment, the control circuit 200 is configured to receive the images from the cameras 210, 212 and generate the new image (e.g., a hemispherical image) based on the received images. The generated image is subsequently transmitted to the controller 102 via the transmitter circuit 224 and the communication link 106. Alternatively, the control circuit 200 may be configured to transmit the images received from the cameras 210, 212 to the controller 102 and the controller 102 is configured to generate the new image based on the received images. Regardless, the images received from the cameras 210, 212 are combined to generate a new image in the process step 256. In one particular embodiment, the new image is a hemispherical image, but in other embodiments, other types of images may be generated. The images received from the cameras 210, 212 may be combined to generate the new image using any suitable algorithm. For example, in some embodiments, the images received from the cameras 210, 212 are appended to each other. In such embodiments, the new image may include an amount of overlap or duplication of visible area. In other embodiments, the images received from the cameras 210, 212 are combined in such a manner that any overlap or copy of the same visible area is reduced or eliminated from the new image. Yet further, in embodiments wherein only a single camera is included in the registration pointer 104, a new image may or may not be generated based on the images received from the single camera. That is, the image received from the single camera may be displayed to the user of the system 100 as discussed below in regard to process step 260.

Next, in process step 258, the controller 102 determines if the user has requested to view the new image generated in process step 256. The user may request to view the generated image by selecting a button displayed on the display 112 (in embodiments wherein the display is a touch screen display) or by providing a command via an input device coupled to the controller 102 such as a keyboard or mouse. Additionally or alternatively, in some embodiments, the input devices 220 of the registration pointer 104 may include an input device 220, such as a button or switch, that the user may select to view the generated image. In such embodiments, when the user selects the appropriate input device 220, the control circuit 200 transmits a request signal via the transmitter 224 and the communication link 106 to the controller 102.

If the user desires to view the generated image, the new image (e.g., a hemispherical image) is displayed to the user in process step 260. The generated image is displayed on the display device 112. As discussed above, in some embodiments, the display 112 is embodied as a heads-up display and the generated image is displayed thereon. The generated image may be displayed as a stand-alone image that the surgeon may use to inspect and/or navigate the anatomy of the patient. Additionally or alternatively, the generated image may be superimposed over the rendered image of the patient's anatomy such that the rendered or calculated anatomy (e.g., a bone) of the patient is comparable to the actual anatomy as displayed in the generated image.

Once the hemispherical image or other generated image(s) has been displayed in process step 260, the controller 102 determines if the user has requested to capture or otherwise store the generated image in process step 262. The user may request to save the generated image by selecting a button displayed on the display 112 or by providing a command via an input device coupled to the controller 102 such as a keyboard or mouse. Additionally or alternatively, in some embodiments, the input devices 220 of the registration pointer 104 may include an input device, such as a button or switch, that the user may select to save the generated image. In such embodiments, when the user selects the appropriate input device 220, the control circuit 200 transmits a request signal to the controller 102 via the transmitter 224 and the communication link 106. In response, the controller 102 stores the generated image in process step 264. The generated image may be stored in, for example, the memory device 110 or in other storage devices such as a hard drive or the like. Once stored, the generated image may be viewed by the surgeon and/or other healthcare provider at any time.

Once the image has been stored in process step 264 or if no request is received to display the image in process step 258 and/or to store the image in process step 262, the algorithm 250 loops back to process steps 254 wherein updated images are received form the cameras 210, 212. In this way, the algorithm 250 may loop through process steps 254, 256, 258, and 260 to receive and display updated generated images based on the updated images received from the cameras 210, 212 such that the stream of images form a video viewable by the surgeon. As the surgeon moves or repositions the registration pointer 104, the generated images are updated and the surgeon may thereby use the video for inspecting and/or navigating the relevant anatomy of the patient.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A registration pointer for registering a bone with a computer assisted orthopaedic surgery system, the registration pointer comprising:
   a handle,
   an elongated shaft extending from the handle, the elongated shaft having a distal end configured to be placed in contact with a bone of a patient,
   a panoramic camera positioned at the distal end,
   a wide-angle camera having a fish-eye lens positioned at the distal end, and
   a sensor array to provide an indication of a location of the registration pointer.

2. The registration pointer of claim 1, further comprising a quartz crystal lens located at the distal end of the elongated shaft.

3. The registration pointer of claim 1, wherein the panoramic camera and the wide-angle camera form a hemispherical camera.

4. The registration pointer of claim 1, wherein the panoramic camera has a horizontal field of view of 360 degrees and a vertical field of view of 120 degrees when the elongated shaft is positioned on a vertical plane.

5. The registration pointer of claim 1, wherein the wide-angle camera has a vertical field of view of 60 degrees when the elongated shaft is positioned on a vertical plane.

6. The registration pointer of claim 1, further comprising a light source.

7. The registration pointer of claim 6, wherein the light source comprises a light emitting diode located in the elongated shaft.

8. The registration pointer of claim 7, wherein the light source is a fiber optic light source.

9. The registration pointer of claim 1, further comprising a transmitter communicatively coupled to the panoramic camera and the wide-angle camera, the transmitter being configured to transmit images received from the cameras.

10. The registration pointer of claim 9, wherein the transmitter is a wireless transmitter.

11. The registration pointer of claim 1, further comprising:
    an input device, and
    a control circuit communicatively coupled to the panoramic camera, the wide-angle camera, and the input device, the control circuit being configured to store an images received from one of the panoramic camera and the wide-angle camera in response to selection of the input device by a user of the registration pointer.

12. The registration pointer of claim 1, further comprising an input device and a control circuit communicatively coupled to the input device, the control circuit being configured to register a location of the bone in response to selection of the input device by a user of the registration pointer.

13. A registration pointer for registering a bone with a computer assisted orthopaedic surgery system, the registration pointer comprising:
    an elongated shaft, the elongated shaft having a distal end configured to be placed in contact with a bone of a patient, a sensor array to provide an indication of a location of the registration pointer, and a hemispherical camera comprising a panoramic camera positioned at the distal end and a wide-angle camera positioned at the distal end.

14. The registration pointer of claim 13, wherein the wide-angle camera includes a fish-eye lens.

15. The registration pointer of claim 13, further comprising a light emitting diode located in the elongated shaft.

16. The registration pointer of claim 13, further comprising a transmitter communicatively coupled to the hemispherical camera and configured to transmit images received from the hemispherical camera.

17. The registration pointer of claim 16, wherein the transmitter is a wireless transmitter.

18. The registration pointer of claim 13, further comprising an input device and a control circuit communicatively coupled to the hemispherical camera and the input device, the control circuit being configured to store an image received from the hemispherical camera in response to selection of the input device by a user of the registration pointer.

19. The registration pointer of claim 13, further comprising an input device and a control circuit communicatively coupled to the input device, the control circuit being configured to register a location of the bone in response to selection of the input device by a user of the registration pointer.

20. A registration pointer for registering a bone with a computer assisted orthopaedic surgery system, the registration pointer comprising:

a handle, an elongated shaft extending from the handle, the elongated shaft having a distal end, a hemispherical camera positioned at the distal end of the elongated shaft, the hemispherical camera comprising: a panoramic camera and a wide-angle camera having a fish-eye lens positioned at the distal end, a quartz crystal lens positioned at the distal end of the elongated shaft, the quartz crystal lens being configured to be placed in contact with a bone of a patient and being positioned such that each of the panoramic camera and the wide-angle camera have a field of view extending through the quartz crystal lens, and a sensor array to provide an indication of a location of the registration pointer.

* * * * *